United States Patent [19]

McAllister et al.

[11] Patent Number: 5,017,488

[45] Date of Patent: May 21, 1991

[54] HIGHLY EFFICIENT DUAL T7/T3 PROMOTER VECTOR PJKF16 AND DUAL SP6/T3 PROMOTER VECTOR PJFK15

[75] Inventors: William T. McAllister, Metuchen, N.J.; John F. Klement, Bethesda, Md.

[73] Assignee: University of Medicine and Dentistry of New Jersey, Newark, N.J.

[21] Appl. No.: 920,327

[22] Filed: Oct. 17, 1986

Related U.S. Application Data

[63] Continuation-in-part of Ser. No. 846,931, Apr. 1, 1986.

[51] Int. Cl.[5] .......................... C12N 7/01; C12N 9/12; C12N 15/10; C12N 15/00
[52] U.S. Cl. ................................. 435/194; 435/320.1; 435/91; 935/31; 935/17
[58] Field of Search .................. 435/172.3, 6, 91, 194, 435/320, 235; 536/27; 935/29, 14, 31, 41, 16, 72, 73

[56] References Cited

U.S. PATENT DOCUMENTS 4,766,072 8/1988 Jendrisak et al. ..................... 435/91

OTHER PUBLICATIONS

Riboprobe-Gene Analysis System Advertising Brochure, Promega Biotec, 1984.
Morris, C. et al, *Gene*, vol. 41, pp. 193-200, 1986.
Riboprobe-Gemini Advertising Brochure, Promega Biotec.
Bluescribe Advertisement, 1985.
BRL Catalogue, 1985.
Bailey, J. et al, *Proc. Natl Acad Sci*, vol. 80, 2814-2818, May, 1983.
McGraw, N. et al, *Nuc. Acids Res.*, vol. 13, p. 6753-6766, Sep. 1985.
Melton, D. et al, *Nuc Acids Res.*, vol. 12, pp. 7035-7056, 1984.
Axelrop, V. et al, *Biochemistry*, vol. 24, pp. 5716-5723, Oct. 1985.
Pharmacia Advertisement, in *Nature*, vol. 317, Oct. 1985.
Adhya, S. et al., *Proc. Natl Acad Sci*, vol. 78, pp. 147-151, 1981.

*Primary Examiner*—Richard A. Schwartz
*Assistant Examiner*—S. L. Nolan
*Attorney, Agent, or Firm*—Weiser & Stapler

[57] ABSTRACT

A dual promoter cassette which has at one end a promoter for T3 RNA polymerase which contains a downstream sequence identical to a naturally occurring T3 promoter sequence and on the other end, a promoter for a phage DNA polymerase other than the T3 RNA polymerase. The recombinant DNA plasmid which includes the promoter. The plasmid is capable of highly efficient transcription of RNA with low concentrations of ribonucleoside triphosphates.

14 Claims, 2 Drawing Sheets

FIG. 1

(a) ABS 63

5'-AATTAACCCTCACTAAAGGGAGAGACG-3'
         -10        +1      +7

(b) 51.5 T3 map unit promoter

5'-AATTAACCCTCACTAAAGGGAGAGACC-3'
         -10        +1      +7

(c) Oligomer No. 7 (of parent application serial No. 846,931)

5'-GACTAATTAACCCTCACTAAAGGGAGATCTG-3'
            -10        +1       +7

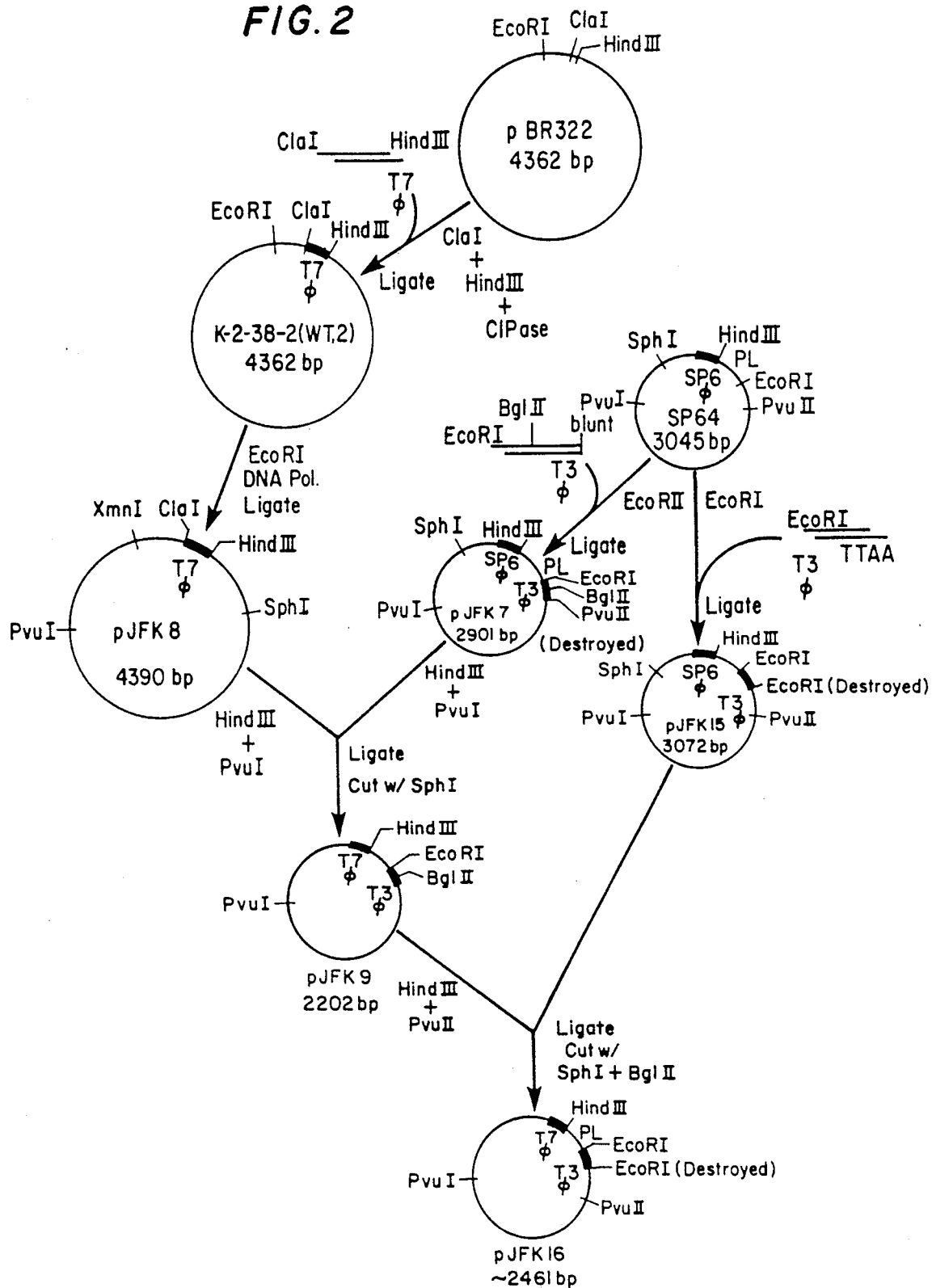

HIGHLY EFFICIENT DUAL T7/T3 PROMOTER VECTOR PJKF16 AND DUAL SP6/T3 PROMOTER VECTOR PJFK15

This is a continuation-in-part of pending patent application Ser. No. 846,931, William T. McAllister, filed on Apr. 1, 1986, entitled Plasmid for the Overproduction of Bacteriophage T3 RNA Polymerase, Transcription Vectors that Carry a Promoter Recognized by this Polymerase, and Application of these Plasmids.

BACKGROUND

In the earlier parent patent application the cloning and expression of a gene that encodes the bacteriophage T3 RNA polymerase, and the use of this RNA polymerase in making synthetic RNA probes were described. This transcription system requires plasmids that carry promoters that are recognized by the T3 RNA polymerase. The most useful type of transcription vectors carry both a T3 promoter and a promoter that is recognized by another phage RNA polymerase, usually that of bacteriophage T7 or bacteriophage SP6. In the earlier patent application the construction of a dual T3/T7 promoter vector designated pJFK9 was described and it was shown that under the conditions specified in the disclosure, that efficient transcription was initiated from the T3 promoter sequence. During subsequent testing of this plasmid, the results of certain experiments suggested that under very specific reaction conditions, the T3 promoter that had been cloned into pJFK9 functioned inefficiently. Specifically, when the concentration of one of the ribonucleoside triphosphates (uridine triphosphate) was lowered to 10 micromolar or less, initiation by the T3 RNA polymerase at the T3 promoter sequence occurred at low levels or was aborted. In reviewing the construction and sequence of pJFK9 it was noted that the sequence of nucleotides that lies downstream from the promoter site contained a thymidine residue at position +7 in the non-transcribed strand. From an initial sequence comparison of all the characterized, naturally occurring T3 promoters it was not obvious that the nucleotide at position +7 played an important role in the initiation of transcription. However, it was subsequently noted that thymidine had not been observed at this location in any of the naturally occurring T3 promoters thus far characterized. (Bailey, J. N. et al, Proc. Nat. Acad. Sci. USA 80:2814-2818 1983, which is incorporated herein by reference). Therefore, it was suspected that the unusual performance of the T3 promoter cloned into pJFK9 might have resulted from this base substitution in the downstream region. To circumvent this problem and to test this hypothesis, a new T3 promoter was synthesized that did not contain this particular change and which had a sequence in the downstream region that corresponded to one of the naturally occurring T3 promoters from positions −17 to +9 that had been previously characterized in the plasmid pJB30 (Bailey, J. N. et al, cited supra). Plasmid pJB30 carries a Taq I restriction fragment containing the strong T3 promoter located at 51.5 T3 map units.

This new synthetic T3 promoter was cloned into the plasmid pSP64 (which also contains a promoter for the bacteriophage SP6 RNA polymerase) resulting in the formation of a dual SP6/T3 promoter plasmid, which is designated pJFK15. The synthetic promoter in pJFK15 was subsequently removed and cloned into the plasmid pJFK9 in place of the synthetic T3 promoter which had previously been present in this plasmid. The new plasmid, which carries both synthetic T7 and T3 promoters, is designated pJFK16.

When the properties of pJFK16 were tested in vitro, it was found that this plasmid had the desired characteristics and performed well even at low concentrations of UTP.

DESCRIPTION OF THE INVENTION

It is an object of the present invention to provide for a dual phage RNA polymerase/promoter system which can be used efficiently in the production of RNA even at low concentrations of ribonucleoside triphosphates.

In accordance with one aspect of the present invention, there is provided a novel vector which includes an improved synthetic promoter for T3 RNA polymerase and a second promoter which is a promoter for the RNA polymerase from bacteriophage T7. This vector also includes a polylinker segment between the two promoters which can accommodate the specific DNA fragment to be transcribed. In accordance with another aspect of the present invention, there is provided another vector which includes the improved synthetic promoter for T3 RNA polymerase and a second promoter for the RNA polymerase from phage SP6.

A better understanding of the present invention as well as other objects and advantages thereof will become apparent upon consideration of the detailed description, especially when taken with the accompanying Figures, wherein:

FIG. 1 is a sequence comparison of the improved T3 promoter (a), the naturally occurring T3 promoter from pJB30 (b) and the T3 promoter from pJFK9 (c);

FIG. 2 is a schematic view of the manufacture of the dual promoter plasmids containing the T3/T7 or T3/SP6 promoter sequences.

To construct these dual promoter plasmids, two oligomers of DNA were synthesized on an Applied Biosystems DNA Synthesizer. These oligomers were designated ABS No. 62 and ABS No. 63. and contain the T3 promoter consensus sequence.

The sequence of ABS No. 62 is

5'-AATTCGTCTCTCCCTTTAGTGAGGGTT-3'

The sequence of ABS No. 63 is

5'-AATTAACCCTCACTAAAGGGAGAGACG-3'

These two oligomers were purified by conventional methods, as described in the parent patent application, and annealed together. The annealed oligomers were then cloned into plasmid pSP64 that had been digested with the restriction enzyme EcoR1. The sequence at the ends of the annealed synthetic oligomer is such that both ends may be ligated into an EcoR1 site in the plasmid, but the recognition sequence for the EcoR1 endonuclease is regenerated at only one end of the inserted DNA. The desired recombinant plasmid has the synthetic oligomer oriented such that the direction of transcription from the T3 promoter is counter clockwise (where transcription from the SP6 promoter is oriented-clockwise). The resulting ligation mixture was cloned into the bacterial host E. coli. HB101, and individual recombinant plasmids in the transformed population were screened for the desired orientation by cleavage of isolated plasmid DNA with the restriction endonucleases HindIII and PvuII; and in another digestion, with EcoRI and PvuII. A recombinant plasmid having the desired orientation releases fragments of 251 bp and 2,821 bp (with the first set of restriction endonucleases) and of 205 bp and 2,867 bp (with the second set of enzymes). A plasmid with the desired characteristics was identified and was designated pJFK15.

To construct plasmid pJFK16, plasmid pJFK9 (described in the previous patent application) was digested with the restriction enzymes HindIII and PvuI, and plasmid pJFK15 was separately digested with the restriction enzymes HindIII and PvuI. The resulting fragments were mixed together and ligated. The desired recombinant (pJFK16) lacks recognition sites for the restriction enzymes SphI and BglII, whereas the two starting plasmids each have sites for one of these enzymes (pJFK9 for BglII and pJFK15 for SphI). Thus, only the recombinant plasmid is resistant to cleavage by these two enzymes.

The resulting mixture of DNA was then transformed into the bacterial host E. coli. HB101, and the population of transformants was screened for the plasmid pJFK16 by digestion with the restriction enzymes HindIII and PvuII and BglII and SphI. The restriction digest gave fragments of 266 and 2108 base pairs. The desired plasmid was identified and tested in vitro for the appropriate characteristics. In addition, the synthetic promoter that had been cloned into pJFK16 was sequenced directly by the methods of Maxam and Gilbert.

The dual promoter vectors of this invention are useful as disclosed in the prior case for various applications. Furthermore, additional applications are known to one skilled in the art. The dual promoter vectors of the invention are especially valuable because efficient initiation by the T3 RNA polymerase at the new T3 promoter occurs at concentrations of ribonucleoside triphosphates (UTP) at and below 10 micromoles. The vectors of the invention which contain the new T3 and T7 transcriptional promoters show an exceptional degree of specificity for their respective polymerases. One skilled in the art will readily know where and how to make use of this new property. For instance, the vectors of the invention are useful to synthesize RNA probes of high sensitivity.

The invention also includes the transformed microorganisms like bacteria which contain the vectors of the invention, and the progeny of such microorganisms. Also within the scope of the invention are kits which include in combination, T7 RNA polymerase, SP6 RNA polymerase, T3 RNA polymerase and the vectors of the invention which include the new strong T3 promoter. As is known, such kits may be supplied in conjunction with a positive control template.

The following examples further illustrate and also disclose a preferred embodiment of the invention disclosed herein. The examples are not to be construed as a limitation on the scope of the invention. One skilled in the art will be able, without undue experimentation, to modify or make variants of the invention as he may desire.

EXAMPLE I

Construction of PJFK15

Ten micrograms of plasmid pSP64 were digested in a reaction volume of 50 ul containing buffer and an excess of 25 units of the restriction endonuclease EcoRI. The buffer contained 100 mM of NaCl, 10 mM of Tris-HCl (pH 7.4), 10 mM of $MgCl_2$, 1 mM of dithiothreitol (DTT), and 0.3 mM of spermidine-HCl. After 1 to 2 hours at 37° C., the reaction mixture was heated to 65° C. for 5 minutes. Calf intestinal alkaline phosphatase (CIPase, Boehringer-Mannheim, 25 units) was added and the reaction mixture was incubated at 37° C. for 30 minutes. To inactivate the CIPase, trinitriloacetic acid, pH 7.7, was added to a concentration of 7 mM and the reaction was heated to 65° C. for 20 minutes. The reaction mixture was extracted with phenol (Maniatis, T., Fritsch, E. F., Sambrook, J., Molecular Cloning: A Laboratory Manual, Cold Spring Harbor Press, Cold Spring Harbor, N.Y., 1982) and the nucleic acids were precipitated by the addition of 2.5 volumes of 95% ethanol at −70° C. for 15 minutes. The pellet was washed twice in 100 ul of 70% ethanol at −20° C., dried in vacuo, and resuspended in 50 ul of 0.01M Tris-HCl, pH 7.4; 1 mm EDTA (TE).

200 nanograms of plasmid pSP64 digested as described above were ligated with about a 20 fold molar excess of synthetic oligomers ABS No. 62 and ABS No. 63 which had been synthesized, purified and annealed as described in the parent patent application in a volume of 20 ul containing 50 mM Tris-HCl pH 7.4, 10 mM $MgCl_2$, 10 mM DTT, 1 mM spermidine-HCl, 1 mM ATP, 0.1 mg/ml bovine serum albumin (BSA), and 0.5 units of T4 DNA ligase (Boehringer-Mannheim) at 16° C. for 12 hours. The reaction mixture was heated to 65° C. for 5 minutes. Twenty nanograms of the reaction mixture were added to 100 ul of competent bacteria (strain HB101) prepared by the method of Hanahan et al (J. Mol. Biol. 166:557–580 1983). Recombinants were screened for the presence of a plasmid generating fragments of 251 and 2,821 base pairs upon digestion with the restriction endonucleases HindIII and PvuII. The resulting plasmid was designated pJFK15. The identity of plasmid pJFK15 was confirmed by screening recombinants using EcoRI and PvuII; a correct construct liberates a 205 bp fragment and a 2,867 bp fragment.

The plasmid was characterized by determining that the plasmid contained SP6 and T3 promoters oriented in opposite directions with a polylinker between the two promoters. This was done by determining that the promoters and the polylinker had the desired level of activity. In addition, a direct sequence determination of the promoter sequence was carried out.

EXAMPLE II

Construction of pJFK16

Plasmid pJFK9 was constructed as described in the parent application, in Example IV. Plasmid pJFK15 was manufactured as described above. One microgram of each plasmid DNA preparation was digested with the restriction endonuclease HindIII in 20 ul of medium salt buffer at 37° C. (Maniatis et al, cited supra). The salt was adjusted to 100 mM sodium chloride and 3.5 units of the restriction endonuclease PvuI were added and incubation was continued at 37° C. for 1 hour. Plasmid pJFK9 was treated with calf intestinal phosphatase as described in Example I. The samples were extracted with phenol, precipitated with ethanol and resuspended in 10 ul of TE as described above.

0.2 ug of each of the digested plasmid DNAs were mixed together and incubated in a ligase reaction of 20 ul containing 0.5 units T4 ligase and the ligase buffer described above at 16° C. for 12 hours and used to transform *E. coli.* HB101 as described previously. Plasmid DNA from resulting transformants was extracted by the rapid alkaline extraction protocol (H. C. Birnboim and J. Doly, Nucleic Acids Research, Vol. 7, page 1513, (1979) A Rapid Alkaline Extraction Procedure for Screening Recombinant Plasmid DNA), and characterized by digestion with SphI and BglII and with PvuII and HindIII.

One plasmid with the desired characteristics of having T3 and T7 promoter sequence on opposite sides of the polylinker was chosen and designated as pJFK16. It was observed that pJFK16 is cut only by PvuII and HindIII giving 266 base pair and 2108 base pair fragments.

We claim:

1. A dual phage RNA polymerase promoter vector having a polylinker with a multiple cloning site, which polylinker is linked at one of its ends to a T3 phage RNA polymerase promoter, which has a consensus sequence recognized specifically by a recombinant-synthesized T3 polymerase and on the other of its ends, to a second phage RNA polymerase promoter, other than the T3 RNA polymerase promoter, the T3 promoter being capable of initiating efficient transcription of DNA at a concentration of ribonucleoside triphosphates of 10 micromolar or less, wherein said promoter does not contain a thymidine residue in the first ten nucleotides downstream of the initiation site, wherein transcription from either of the phage promoters proceeds toward the other promoter and in a direction opposite from the direction of transcription of the other phage promoter and the phage polymerase capable of transcription from said promoters is specific and does not recognize the other phage promoter.

2. The dual RNA polymerase promoter vector of claim 1 wherein the second promoter is selected from the group consisting of phage RNA polymerase promoters phage T7 and SP6.

3. The dual RNA polymerase promoter vector of claim 2 wherein the second promoter is a RNA polymerase promoter.

4. The dual phage RNA polymerase promoter vector of claim 1 wherein the consensus sequence is contained in a nucleotide sequence selected from the group of sequences consisting of AATTCGTCTCTCCCTTTAGTGAGGGTT and

AATTAACCCTCACTAAAGGGAGAGACG.

5. The dual phage RNA polymerase promoter vector of claim 4 wherein the sequence is AATTAQACCCTCACTAAAGGGAGAGACG.

6. The dual phage RNA polymerase promoter vector of claim 1 wherein the concentration of a ribonucleoside triphosphate necessary for efficient transcription is less than 10 micromolar.

7. A recombinant DNA vector which comprises a polylinker sequence having linked to one of its ends a T3 phage RNA polymerase promoter which has a consensus sequence recognized specifically by a recombinant-synthesized T3 polymerase and at the other of its ends, a second phage RNA polymerase promoter, wherein said second promoter is a promoter other than a T3 phage RNA polymerase promoter and a DNA sequence inserted in the polylinker sequence, the respective promoters being in opposite orientation, the recombinant DNA vector being capable of transcription of DNA to produce RNA strands complementary to either one of the strands of the inserted DNA sequence when there is supplied to the vector a phage promoter-specific polymerase, the T3 promoter being capable of initiating efficient transcription of DNA at low concentrations of ribonucleoside triphosphates of 10 micromolar or less, wherein said promoter does not contain a thymidine residue in the first ten nucleotides downstream of the initiation site, wherein transcription from either of the phage promoters proceeds toward the other promoter and in a direction opposite from the direction of transcription of the other phage promoter and the phage polymerase capable of transcription from said promoters is specific and does not recognize the other phage promoter.

8. The recombinant DNA vector of claim 7 wherein the second promoter is a T7 RNA polymerase promoter.

9. The recombinant DNA vector of claim 7 which lacks restriction sites for enzymes SphI and BglII, whereby the vector is resistant to cleavage by these two enzymes.

10. The recombinant DNA vector of claim 7 wherein the consensus sequence is contained in a nucleotide sequence selected from the group of sequences consisting of:

AATTCGTCTCTCCCTTTAGTGAGGGTT and

AATTAACCCTCACTAAAGGGAGAGACG.

11. The recombinant DNA vector of claim 10 wherein the sequence is AATTAACCCTCACTAAAGGGAGAGACG.

12. The recombinant DNA vector of claim 7 wherein the concentration of a ribonucleoside triphosphate necessary for efficient transcription is less than 10 micromolar.

13. A kit for genetic applications especially for transcription of DNA to synthesize RNA transcripts complementary to either strand of a DNA sequence, which kit comprises in combination the following components: a recombinant-synthesized T3 RNA polymerase, a recombinant-synthesized T7 RNA polymerase and a dual promoter transcription vector having a T3 phage RNA promoter for said T3 polymerase and a T7 phage RNA promoter for said T7 polymerase, the respective promoters being linked at opposite ends of the polylinker and in opposite orientation, said T3 having a consensus sequence recognized by T3 polymerase, wherein the first ten nucleotides downstream of the initiation site do not contain a thymidine residue, with which kit, components and cleaved vector, RNA transcripts can be synthesized that are complementary to either one of the strands of cloned DNA sequence, the T3 promoter being capable of efficient transcription of DNA at low concentrations of ribonucleoside triphosphates of 10 micromolar or less, wherein transcription from either of the phage promoters proceeds toward the other promoter and in a direction opposite from the direction of transcription of the other phage promoter and the phage polymerase capable of transcription from said promoters is specific and does not recognize the other phage promoter.

14. The kit of claim 13 wherein the concentration of a ribonucleoside triphosphate necessary for efficient transcription in less than 10 micromolar.

* * * * *